US009642685B2

(12) United States Patent
Brodkin (10) Patent No.: US 9,642,685 B2
(45) Date of Patent: May 9, 2017

(54) DIGITAL TECHNOLOGIES FOR PLANNING AND CARRYING OUT DENTAL RESTORATIVE PROCEDURES

(75) Inventor: Dmitri Brodkin, Livingston, NJ (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 1872 days.

(21) Appl. No.: 10/893,721

(22) Filed: Jul. 16, 2004

(65) Prior Publication Data

US 2005/0070782 A1      Mar. 31, 2005

Related U.S. Application Data

(60) Provisional application No. 60/488,231, filed on Jul. 17, 2003.

(51) Int. Cl.
| | |
|---|---|
| *A61B 5/05* | (2006.01) |
| *A61C 19/045* | (2006.01) |
| *A61C 13/00* | (2006.01) |
| *A61C 9/00* | (2006.01) |

(52) U.S. Cl.
CPC ........ *A61C 19/045* (2013.01); *A61C 13/0004* (2013.01); *A61C 9/004* (2013.01)

(58) Field of Classification Search
USPC .................. 600/407, 427; 382/103; 356/620; 433/24
See application file for complete search history.

(56) References Cited

U.S. PATENT DOCUMENTS

| | | |
|---|---|---|
| 4,294,544 A | 10/1981 | Altschuler et al. |
| 4,575,805 A | 3/1986 | Moermann et al. |
| 4,611,288 A | 9/1986 | Duret et al. |
| 4,663,720 A | 5/1987 | Duret et al. |
| 4,821,200 A | 4/1989 | OBerg |
| 4,837,732 A | 6/1989 | Brandestini et al. |

(Continued)

FOREIGN PATENT DOCUMENTS

| | | |
|---|---|---|
| DE | 19524855 A1 | 1/1997 |
| EP | 0837659 B1 | 11/1999 |

OTHER PUBLICATIONS

Definition of Dental Appliance from thefreedictionary.com.*

(Continued)

*Primary Examiner* — Jonathan Cwern
(74) *Attorney, Agent, or Firm* — Wood Herron & Evans LLP (57) ABSTRACT

A method and system for the fabrication of dental articles includes at least two imaging and measuring devices, which measure and provide images of the internal and external structure of intra-oral objects in a patient's oral cavity. The outputs from these devices are linked so that the descriptions of the intra-oral objects and features, oral cavity and surrounding bone structure are stored in a system of reference positions. The system of reference positions functions as a "global positioning device" registering locations and orientations of the measuring and imaging device or probe relative to the intra-oral objects and bone structure and orientations of the resulting individual frames or scans in the global system of coordinates. Three-dimensional images, scans and/or maps of the oral cavity obtained from each device are pieced together to generate solid three-dimensional models of the intra-oral objects.

32 Claims, 5 Drawing Sheets

(56) References Cited

U.S. PATENT DOCUMENTS

| | | | |
|---|---|---|---|
| 4,964,770 A | 10/1990 | Steinbichler et al. | |
| 5,011,405 A * | 4/1991 | Lemchen | 433/24 |
| 5,027,281 A | 6/1991 | Rekow et al. | |
| 5,076,687 A | 12/1991 | Adelson | |
| 5,184,306 A | 2/1993 | Erdman et al. | |
| 5,237,998 A | 8/1993 | Duret et al. | |
| 5,257,184 A | 10/1993 | Mushabac | |
| 5,339,154 A | 8/1994 | Gassler et al. | |
| 5,343,391 A | 8/1994 | Mushabac | |
| 5,359,511 A | 10/1994 | Schroeder et al. | |
| 5,440,393 A | 8/1995 | Wenz | |
| 5,569,578 A | 10/1996 | Mushabac | |
| 5,587,912 A | 12/1996 | Andersson et al. | |
| 5,604,817 A | 2/1997 | Massen et al. | |
| 5,649,032 A | 7/1997 | Burt et al. | |
| 5,706,128 A | 1/1998 | Greenberg | |
| 5,742,294 A | 4/1998 | Watanabe et al. | |
| 5,842,858 A * | 12/1998 | Truppe | 433/69 |
| 5,851,115 A | 12/1998 | Carlsson et al. | |
| 5,880,962 A | 3/1999 | Andersson et al. | |
| 5,933,664 A | 8/1999 | Bacs, Jr. | |
| 6,008,905 A | 12/1999 | Breton et al. | |
| 6,020,993 A | 2/2000 | Greenberg | |
| 6,068,482 A | 5/2000 | Snow | |
| 6,078,701 A | 6/2000 | Hsu et al. | |
| 6,266,453 B1 | 7/2001 | Hibbard et al. | |
| 6,318,995 B1 | 11/2001 | Sachdeva et al. | |
| 6,341,952 B2 | 1/2002 | Gaylo et al. | |
| 6,364,660 B1 | 4/2002 | Durbin et al. | |
| 6,386,867 B1 | 5/2002 | Durbin et al. | |
| 6,402,707 B1 | 6/2002 | Ernst | |
| 6,413,084 B1 | 7/2002 | Rubbert et al. | |
| 6,414,708 B1 | 7/2002 | Carmeli et al. | |
| 6,476,803 B1 | 11/2002 | Zhang et al. | |
| 6,512,994 B1 | 1/2003 | Sachdeva | |
| 6,542,249 B1 | 4/2003 | Kofman et al. | |
| 6,648,640 B2 | 11/2003 | Rubbert et al. | |
| 6,657,796 B2 | 12/2003 | Greenberg | |
| 6,671,539 B2 | 12/2003 | Gateno et al. | |
| 6,738,508 B1 | 5/2004 | Rubbert et al. | |
| 6,744,914 B1 | 6/2004 | Rubbert et al. | |
| 6,771,809 B1 | 8/2004 | Rubbert et al. | |
| 6,819,318 B1 | 11/2004 | Geng | |
| 6,845,175 B2 | 1/2005 | Kopelman et al. | |
| 6,882,744 B2 | 4/2005 | Oosawa | |
| 6,891,671 B1 | 5/2005 | Greenberg | |
| 6,996,430 B1 * | 2/2006 | Gilboa et al. | 600/407 |
| 7,010,150 B1 | 3/2006 | Pfeiffer et al. | |
| 7,027,642 B2 | 4/2006 | Rubbert et al. | |
| 7,084,868 B2 | 8/2006 | Farag et al. | |
| 2002/0059049 A1 | 5/2002 | Bradbury et al. | |
| 2002/0061495 A1 * | 5/2002 | Mault | 433/215 |
| 2002/0064759 A1 | 5/2002 | Durbin et al. | |
| 2002/0143276 A1 | 10/2002 | Ernst | |
| 2002/0183959 A1 * | 12/2002 | Savill et al. | 702/150 |
| 2003/0114778 A1 * | 6/2003 | Vilsmeier et al. | 600/585 |
| 2003/0204150 A1 * | 10/2003 | Brunner | 600/590 |
| 2004/0157188 A1 * | 8/2004 | Luth et al. | 433/75 |
| 2004/0265770 A1 * | 12/2004 | Chapoulaud et al. | 433/24 |
| 2005/0048432 A1 * | 3/2005 | Choi et al. | 433/24 |
| 2005/0163342 A1 * | 7/2005 | Persky | 382/103 |
| 2006/0079981 A1 * | 4/2006 | Rubbert et al. | 700/98 |
| 2006/0286501 A1 * | 12/2006 | Chishti et al. | 433/24 |

OTHER PUBLICATIONS

Definition of Dental Restoration from thefreedictionary.com.*
Elsayed E. Hemayed, Sameh M. Yamany and Aly A. Farag, Three Dimensional Model Building in Computer Vision With Orthodontic Applications, Nov. 1996, 27 pages.
Rekow, D., "Computer-aided design and manufacturing in dentistry; A review of the state of the art", Journal of Prosthetic Dentistry, vol. 58, Oct. 1987, pp. 513-516.
Sameh M. Yamany and Aly A. Farag, A System for Human Jaw Modeling Using Intra-Oral Images, Article, 4 pages, Computer Vision and Image Processing Laboratory, University of Louisville, Department of Electrical Engineering, Louisville, KY; 1998.
Hossam Hassan, Ayman El-Baz, Aly A. Farag, Allan G. Farman, D. Tasman, and William M. Miller, A Complete Volumetric 3D Model of the Human Jaw, 6 pages, Computer Vision and Image Processing Lab, University of Louisville, Louisville, KY; 2005.

* cited by examiner

DIGITAL TECHNOLOGIES FOR PLANNING AND CARRYING OUT DENTAL RESTORATIVE PROCEDURES

CROSS-REFERENCE TO RELATED APPLICATIONS

This application claims priority to U.S. Provisional Application No. 60/488,231, filed Jul. 17, 2003, entitled Method of Manufacture of Dental Restorations, which is incorporated herein by reference.

FIELD OF THE INVENTION

This invention relates to a method and system of quantitative imaging, rapid prototyping and reconstruction/restoration of intra-oral objects and surrounding bone structure for primary use in the field of dentistry for treating dental patients as well as to a method for training and educating dental professionals.

BACKGROUND OF THE INVENTION

The fabrication of current all-ceramic dental restorations often requires extensive labor and time and the proficiency of highly skilled technicians. Many state-of-the-art dental restorations reveal a sense of artistry that can typically only be achieved manually or "by hand." While aesthetics are preserved with this process, microstructural inhomogeneities may appear, affecting strength and reliability. The industry has attempted to automate this process by, for example, pressing crowns. Although pressable crowns reduce some of the skill time required, about two hours of concerted effort is necessary to complete a crown. Pressed crowns may also suffer from similar strength and reliability problems typical of "hand made" crowns.

In current practice, an impression is taken by a dentist and sent to a dental lab where a stone model is cast from the impression. A stone model is used to wax-up copings and frameworks to be invested in a refractory investment for subsequent casting or pressing. Materials used in this multi-step procedure (impression material, stone, wax, refractory investment) have their individual shrinkage/expansion characteristics adding to the "propagation" error and variability of results. Shade is taken by the dentist by comparing the patient's teeth to his shade guide and communicating this subjective evaluation to the dental laboratory. The dental laboratory fabricates the dental restoration and compares its shade to yet another shade guide. This procedure is extremely subjective and prone to error due to the inconsistencies between the shade guides.

In current automated procedures, there remain problems involving the accuracies of intra-oral scanning due to the rigorous requirements of the contact and optical digitizers, which both utilize precision immobile reference systems. Moreover, subgingival surfaces, undercuts and, very frequently, occlusal surfaces cannot be extrapolated from optical data. Therefore, even state-of-the art CAD/CAM methods (e.g., Procera®, Cercon®, Lava®, and Cerec® methods) may require casting of stone models from impressions, stones or wax models.

Devices integrating outputs from multiple sources are already in use in other areas of medicine such as combined magnetic resonance imaging (MRI) and computed axial tomography (CAT) devices. Attempts are being made to combine panoramic X-ray devices that provide accurate 3D images of jaw bones with solid-free form manufacturing machines that produce scaffolds for jaw bone reconstruction.

It would be beneficial to eliminate or reduce conventional steps used in current dentistry techniques such as the taking of impressions and the casting of models.

SUMMARY OF THE INVENTION

The invention combines, into one system, at least two imaging and measuring devices, which measure and provide images of the internal and external structure of intra-oral objects in a patient's oral cavity. The outputs from these devices are linked so that the descriptions of the intra-oral objects and features, oral cavity and surrounding bone structure are stored in a system of reference positions. Virtual Articulator Software may be used to visualize, plan and design the dental procedures and restorations. The system of reference positions functions as a "global positioning device" registering locations and orientations of the measuring and imaging device or probe relative to the intra-oral objects and bone structure and orientations of the resulting individual frames or scans in the global system of coordinates. Three-dimensional images, scans and/or maps of the oral cavity obtained from each device are pieced together and used by Virtual Articulator Software of this invention to generate solid three-dimensional models of the intra-oral objects, including subgingival surfaces and occlusal surfaces. These solid three-dimensional models are used to generate slice-by-slice software instructions for rapid-prototyping and/or CAD/CAM devices employed to fabricate physical models, cores and frameworks for dental restorations.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

This invention relates to a method and system of quantitative imaging, rapid prototyping and reconstruction/restoration of intra-oral objects and surrounding bone structure (mandible and maxilla) for primary use in the field of dentistry for treating dental patients as well as for training and educating dental professionals. This invention obviates the need to take impressions, cast stone models and use conventional dental articulators. U.S. Pat. No. 6,402,707 is directed to a method and system for real time intra-orally acquiring and registering there-dimensional measurements and images of intra-oral objects and features and is hereby incorporated by reference.

In accordance with the invention, the system comprises a multitude of devices which are interconnected to produce data and results in order to fabricate dental restorative devices and dental training and educational devices. The system includes one or more imaging and measuring devices, a global positioning system and software, firmware and/or hardware devices.

It is preferable that the system includes at least two imaging and measuring devices. The imaging and measuring devices are used to measure internal and topographical features of the intra-oral component in a patient's oral cavity. Examples of imaging and measuring devices for imaging and measuring the internal features of the intra-oral component include, but are not limited to, three-dimensional (3D) X-ray devices, magnetic resonance imaging (MRI) devices, and Computed Aided Tomography (CAT) Scan devices. Examples of imaging and measuring devices for imaging and measuring the surface or external features of the intra-oral component include, but are not limited to, intra-oral videocameras, optical scanners, optical digitizers, and spectrophotometers.

The imaging and measuring devices measure and record the internal and external information. The internal information includes the density and internal structure of the intra-oral component. The external information includes the surface appearance and features.

In order to provide very precise and accurate data, the imaging and measuring devices take many measurements of the intra-oral component. These measurements must then be coordinated to provide a complete image of the intra-oral component. A "reference system" is linked to the imaging and measuring devices to organize and coordinate the data so that an overall image can be provided.

This reference system functions as a "global positioning device" and registers the location and orientation of the measuring and imaging devices, which may or may not include a probe, relative to the intra-oral objects and/or bone structure. It also provides the orientation of the resulting individual frames or scans in a global system of coordinates. The global positioning or reference system is based on a series of reference position indicator devices. Three types of reference positions indicator devices used in the reference system are: Type 1 (analogous to a ground unit or tower) reference position indicator devices are attached rigidly to intra-oral objects inside the oral cavity of a dental patient (e.g. glued to the tooth); Type 2 (analogous to a receiver or an automobile) reference position indicator devices are attached rigidly to a probe or mobile measuring and imaging device moving inside or outside the oral cavity of a dental patient; and Type 3 (analogous to a satellite) reference position indicator devices are attached rigidly to a structural element within a space enclosing both the dental patient and the measuring/imaging devices (e.g. attached to a part of the structure containing the dental office such as a wall in the dental office). Some of the many novel features of this invention are the number and combination of reference position indicator devices in the system. The Type 2 reference position indicator devices are positioned on movable measuring and imaging devices. The Type 1 and Type 3 reference position indicator devices are positioned on stationary components, although the Type 3 reference position indicator devices, which are located in the patient's oral cavity on intra-oral objects, may unintentionally move if the patient moves. The occurrence of such movement will be compensated for due to the presence of the Type 1 and Type 2 reference position indicator devices, which will calculate and compensate for the change in position of the Type 2 reference position indicator devices.

The reference indicator position devices are registration devices based on passive devices or active devices comprising microdevices, controllers, transducers, transceivers, sensors, and tracking devices including at least one, preferably a plurality, of components 38 selected from the group consisting of registration signal sensors, registration signal receivers, registration signal transmitters, and registration signal transceivers.

As stated above, Type 1 reference position indicator devices are rigidly attached to one or more intra-oral features. Type 2 reference position indicator devices are attached to probes of the measuring and imaging devices and Type 3 reference position devices are attached to walls or equipment which is stationary in the dentist's office.

The outputs from the reference position devices are linked to a data collection device such as a Position Signal Programming/Processing Unit (PSPPU) for monitoring, calculating and recording the location of the reference positions relative to the global system of coordinates. Three-dimensional images, scans and/or maps of the oral cavity obtained from each device are pieced together and used by Virtual Articulator Software of this invention to generate solid three-dimensional models of the intra-oral objects, including subgingival surfaces and occlusal surfaces. These solid three-dimensional models are used to generate slice-by-slice software instructions for rapid-prototyping and/or CAD/CAM devices employed to fabricate physical models, cores and frameworks for dental restorations as well as more sophisticated prosthetics and repair including bone prosthetics and TMJ repairs including animating temporomandibular joint movements comprises generating mesh and/or performing stress analysis.

Figure 1:
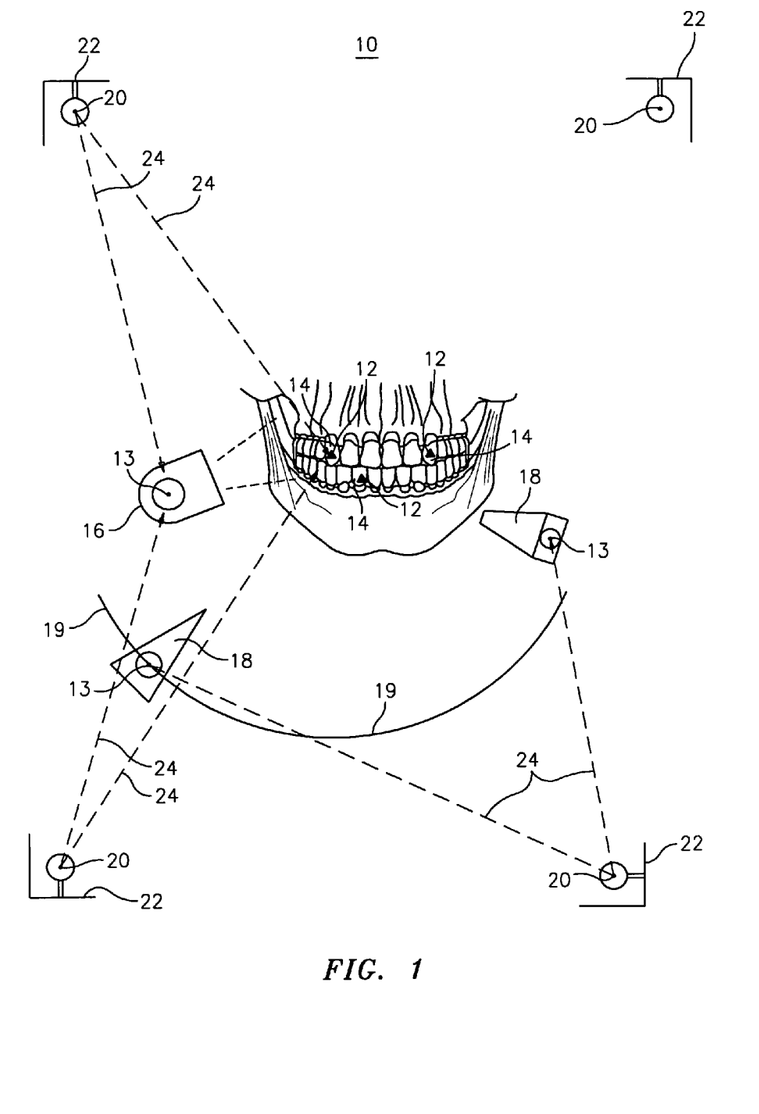
FIG. 1 is a schematic representation of the imaging, measuring and global positioning system described herein.

Reference is now made to FIG. 1, which shows the system 10 in place. The function and purpose of the reference system of the present invention can be explained by analogy to a satellite guided global positioning system somewhat similar to the one used in automobiles wherein the reference position device of Type 1 is an analog of a ground unit or tower, the reference position device of Type 2 is an analog of an automobile or a receiver and the reference position device of Type 3 is an analog of a satellite. For example, while an automobile (probe or mobile measuring/imaging device) is moving relatively to a tower (intra-oral object with reference position attached, e.g. transducer glued to the tooth) relative positions and movements of both are continuously monitored and recorded by a satellite (reference position e.g. transducer attached to the structure of the room) in terms of global coordinates.

Type 1 reference position device 12 is shown at three locations on a plurality of teeth 14 in a patient's oral cavity. Device 12 is an intra-oral fixed global registration device and can be a passive device or a microdevice that includes at least one, preferably a plurality of components such as, but not limited to registration signal sensors, registration signal receivers, registration signal transmitters, and registration signal transceivers, in addition to other types of transducers, trackers or transceivers.

Type 2 reference position device 13 is located on a measuring and imaging device 16 for measuring the topographical features of the intra-oral objects (in this instance, teeth 14) such as, but not limited to, intra-oral videocameras, optical scanners, optical digitizers, and spectrophotometers. Also included in the system is another Type 2 reference position device 13 located on a second measuring and imaging device 18, which measuring and imaging device is used for measuring the internal properties, such as the density, of teeth 13. Device 18 may be, but is not limited to, a 3D X-ray device, an MRI device, or a CAT Scan device. Line 19 denotes the span of the measuring area of device 18.

Type 3 reference position device 20 is located in four places (e.g., the walls) inside the confines of a dentist's office represented by 22. Device 20 is a stationary registration device or network of devices that is closely associated with the global reference system and tracks reference positions of Types 1 and 2 reference position devices even if they are not in the same field of view from each other and "don't see each other." Examples of device 20 include, but are not limited to, at least one, preferably a plurality, of components such as registration signal sensors, registration signal receivers, registration signal transmitters, and registration signal transceivers, other types of transducers, trackers or transceivers.

Devices 20 are linked to devices 12 and 13 as shown by dotted lines 24. The devices may be linked according to a wired or wireless communications mode. Devices 12, 13 and 20 register the location, distance, position and all information necessary for the measuring and imaging data received from devices 16 and 18. The data may be interpolated using one or more software, hardware and firmware devices such as, but not limited to, a PSPPU, Central Programming/Processing Unit (CPPU) and Virtual Articulator Software.

The reference system of the present invention is designed, configured and operated according to a category of mechanisms used for measuring distances and recording positions of objects and features selected from the group consisting of electrical, electronic, electro-mechanical, electro-optical, electromagnetic, radar, magnetic, magneto-mechanical, magnetic resonance, acoustic, ultrasound, sonar, photo-acoustic, telemetry, hybrid and combination mechanisms, thereof. The reference positions can be active, i.e. communicating with each other and with the PSPPU and/or passive, i.e. only responding to electric, electromagnetic, magnetic etc. stimulation from other units such as in a Linear Variable Digital transformer (LVDT). Three-dimensional images, scans and/or maps of the oral cavity obtained from each measuring and imaging device are fed into the Central Programming/Processing Unit (CPPU) together with three-dimensional scans generated by three-dimensional panoramic X-rays.

Figure 2:
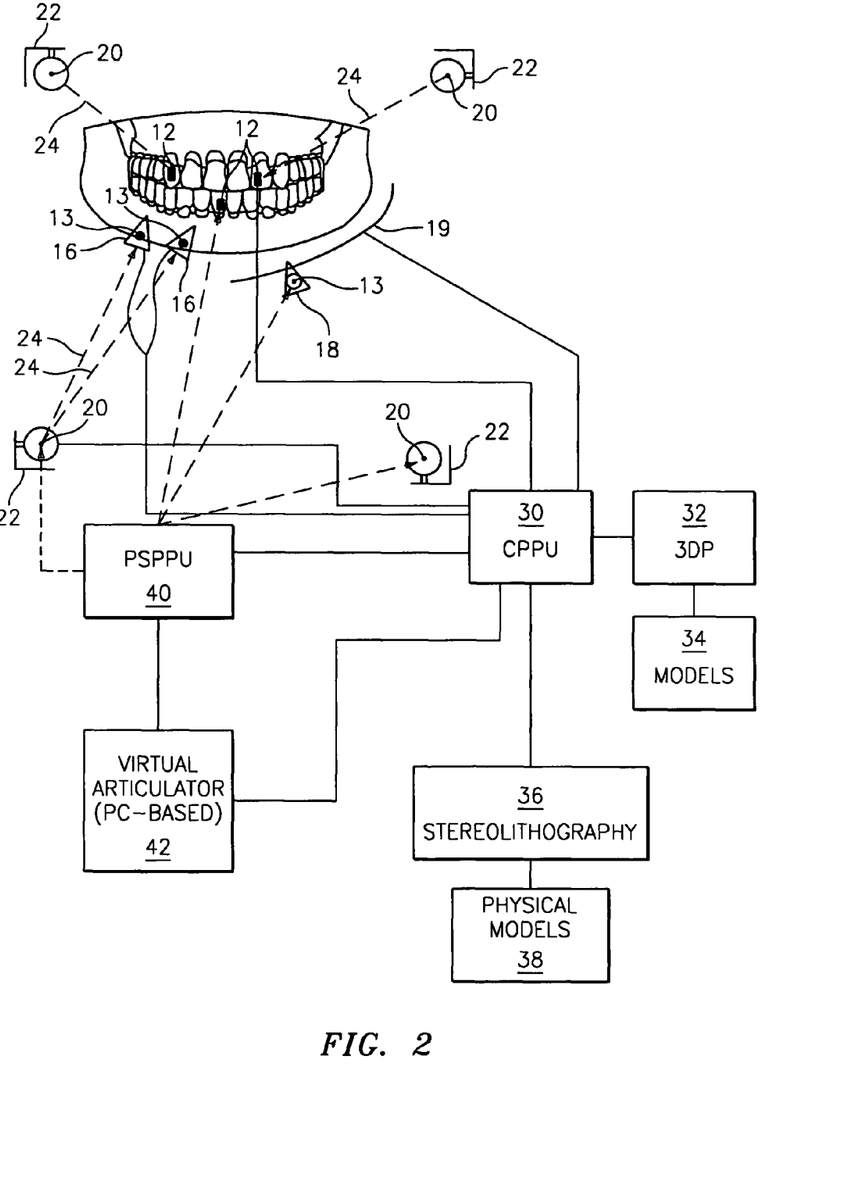
FIG. 2 is schematic representation of the imaging, measuring, global positioning, and free-form fabrication system described herein.

FIG. 2 is a schematic representation showing a CPPU 30 integrating optical and other input and superimposing them with X-ray scans. The CPPU 30 is linked to devices 12, 13, 16, 18 and 20. The CPPU processes the data received from the devices and interpolates it into imaging data for the fabrication of physical models using free form fabrications methods such as three-dimensional printing or stereolithography. Box 32 represents a 3-D printing apparatus that produces models 34. Box 36 represents a stereolithography apparatus that produces models 38. A PSPPU 40 is also shown connected to CPPU 30 and devices 12, 13, 16, 18 and 20. Virtual Articulator Software 42 of this invention is used to generate solid three-dimensional models 34 and 38 of the intra-oral objects, including subgingival surfaces and occlusal surfaces fabricated using the free form fabrication devices 32 and 36.

Figure 3:
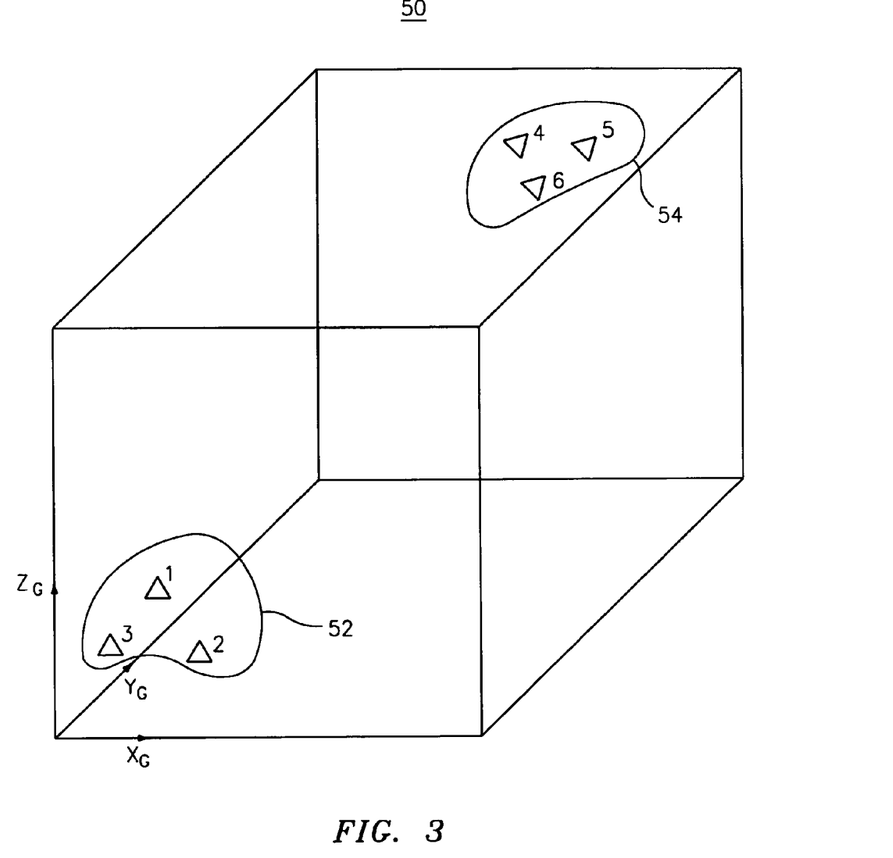
FIG. 3 is a representation of reference points in a global system of coordinates received from a reference position device.
Figure 4:
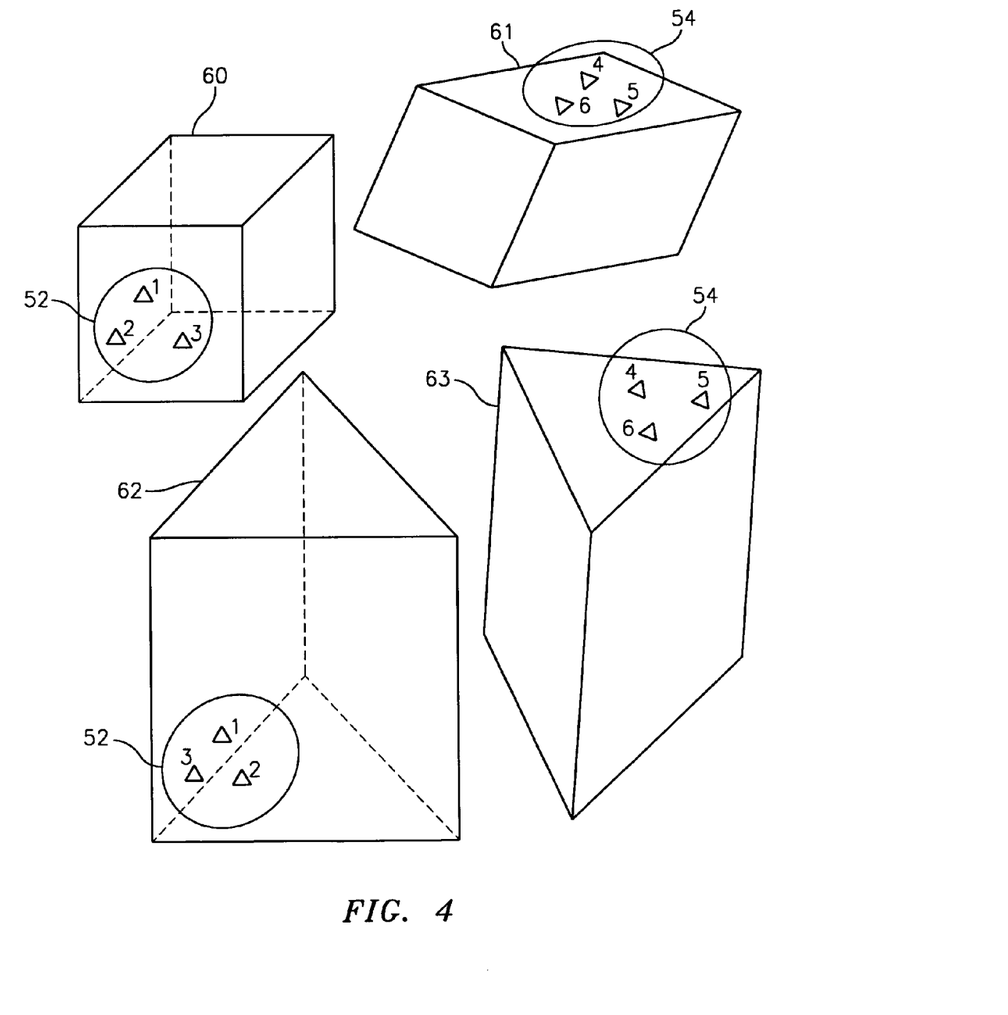
FIG. 4 is a representation of a reference points in a global system of coordinates received from a reference position device.
Figure 5:
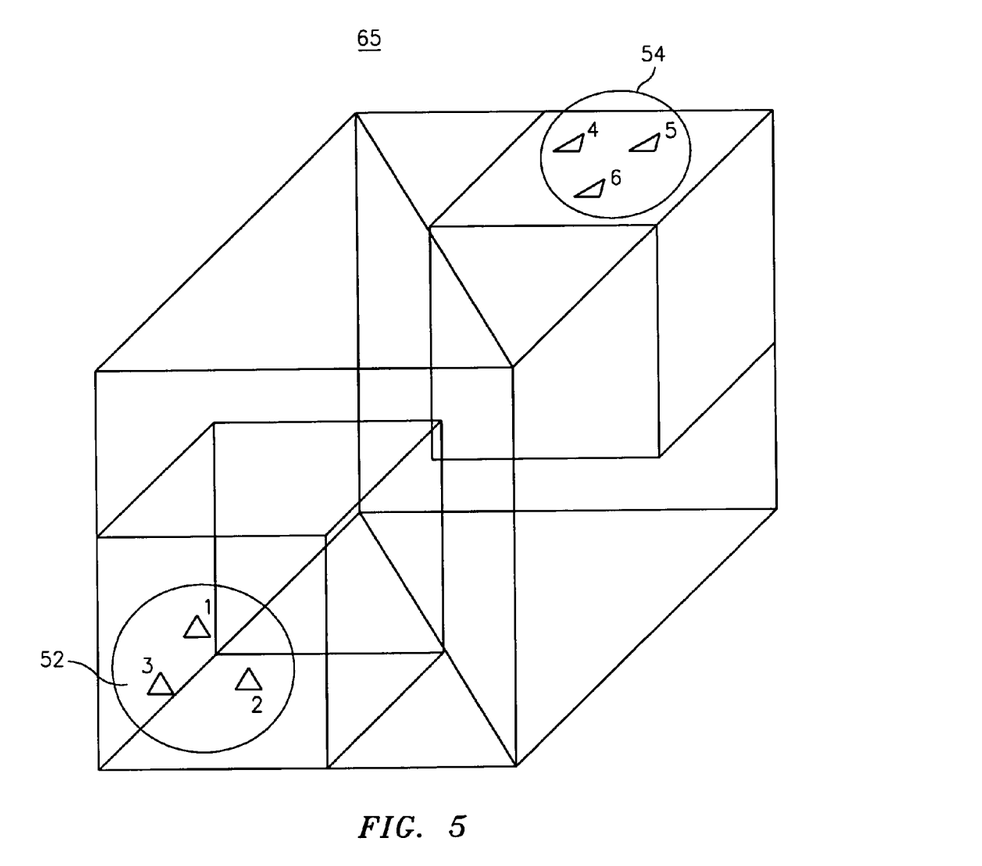
FIG. 5 is a representation of assembled reference points in a global system of coordinates received from a reference position device.

Orientation of each scan recorded by the measuring and imaging devices can be calculated by using a global system of coordinates as shown in FIGS. 3, 4 and 5. FIG. 3 show a global space 50 defined in terms of a global system of coordinates $X_G$, $Y_G$, and $Z_G$. A series of reference points 52 and 54 defined by 1, 2 and 3 and 4, 5 and 6, respectively, are shown in global space 50. Reference points 52 and 54 are positions received from the Type 1 reference position device used herein.

FIG. 4 shows a series of global spaces 60, 61, 62 and 63 showing reference points 52 and 54 as received from the Type 1 reference position device used herein. FIG. 5 shows global space 65 with assembled scans of reference points 52 and 54.

In one of the embodiments of this invention the procedure for piecing together or orienting scans is based on the approach that the same reference points are visible in optical scans as well as in X-ray scans. It is a unique feature of the present invention that superimposition of optical and X-ray data allows one to interpolate and/or accurately reconstruct subgingival surfaces and margins as well as undercuts. Composite data is used by the Virtual Articulator Software of this invention to generate solid three-dimensional models of the intra-oral objects, including subgingival surfaces and occlusal surfaces. These solid three-dimensional models are used to design dental restorations and generate slice-by-slice software instructions for rapid-prototyping and/or CAD/CAM devices employed to fabricate physical models, cores and frameworks for dental restorations.

In one of the preferred embodiments of this invention stereolithography is used to fabricate dental models and three-dimensional printing is used to fabricate metal frameworks, composite and all-ceramic cores of dental restorations using metal, composite or ceramic powder beds. In another preferred embodiment CAD/CAM is used to fabricate metal frameworks, composite and all-ceramic cores of dental restorations. In yet another embodiment not only fabrication of frameworks/cores is automated but manufacturing of outer shells of dental restorations is automated as well. Solid-free form fabrication methods such as three-dimensional printing or fused deposition modeling are used to manufacture outer shells of dental restorations from polymer composites or porcelain. The required shade is achieved by layering pre-shaded materials or created by techniques similar to water-marks in three-dimensional space. Frameworks/cores and outer shells are then bonded together.

In another embodiment of the present invention, the Virtual Articulator Software in addition to solid three-dimensional modeling capabilities allows one to animate temporomandibular joint (TMJ) movements and has in-built finite element analysis (FEA) capabilities to generate mesh and perform stress analysis.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of manufacturing a physical model, core, or framework for a dental restoration comprising:
    (a) establishing one or more first reference position(s) on one or more of a patient's teeth such that all of the patient's teeth can be at least partially imaged;

(b) establishing one or more second reference positions on probes of one or more imaging/measuring devices;

(c) establishing one or more third reference positions outside an oral cavity of the patient and within a signal receiving distance from the first and second reference positions;

(d) linking the first, second and third reference positions in a reference coordinate system;

(e) scanning the patient's teeth with a first imaging/measuring device to characterize a surface of at least a portion of each tooth without impressions or cast models;

(f) scanning the patient's teeth with a second imaging/measuring device to characterize an internal structure of the teeth;

(g) retrieving image data from all the imaging/measuring devices and storing the image data in a data collection device;

(h) repeating steps (d), (e), (f), and (g);

(i) determining an orientation of the image data from each individual scan from each individual device in the reference coordinate system based on the first, second and third reference positions and superimposing the image data to provide a virtual model of the patient's teeth;

(j) using the virtual model of the patient's teeth, designing the dental restoration by generating the physical model, core or framework for the new dental restoration.

2. The method of claim 1 further comprising scanning the patient's teeth with a third imaging/measuring device to characterize characteristics of the teeth.

3. The method of claim 2 wherein the characteristics comprise color, surface texture, visual appearance and internal structure.

4. The method of claim 1 wherein reference positions are established on teeth, implants, posts, or existing restorations, implanted in the bone or attached to an oral cavity of the patient.

5. The method of claim 4 wherein the new dental restoration comprises crowns and bridges.

6. The method of claim 4 wherein the new dental restoration comprises devices for monitoring of the integrity of existing dental restoration, health of the existing dental restoration, oral environment and density of the adjacent/surrounding tissues.

7. The method of claim 4 further comprising using virtual articulator software and solid three-dimensional modeling equipment configured to animate temporomandibular joint movements.

8. The method of claim 7 wherein animating temporomandibular joint movements comprises generating mesh and/or performing stress analysis.

9. A system for manufacturing a physical model, core, or framework for a dental restoration comprising:

a first imaging and measuring device operative to measure and generate an image of a surface appearance of a patient's teeth without impressions or cast models;

a second imaging and measuring device operative to measure and generate an image of an internal structure of the patient's teeth;

a positioning system;

a data collection device for storing image data received from the first and second imaging and measuring devices and position data received from the positioning system;

a processor configured to process the image and position data stored in the data collection device; and a rapid prototyping or CAD/CAM machine configured to create a three dimensional shape of the dental restoration, wherein the positioning system includes a series of reference position indicators and a position signal programming/processing unit for monitoring, calculating and recording the location of the reference position indicators in a reference system, and wherein the processor is configured to process the image and position data stored in the data collection device by:

superimposing the image data received from the first imaging and measuring device on the image data received from the second imaging and measuring device, wherein the image data received from the first and second imaging and measuring devices is oriented in the reference system using the series of reference position indicators, and wherein the processor is further configured to use the image data stored in the data collection device to generate slice-by-slice software instructions for the rapid-prototyping or CAD/CAM machine.

10. The system of claim 9 wherein the first imaging and measuring device comprises an intra-oral video camera, an optical scanner, an optical digitizer or a spectrophotometer.

11. The system of claim 9 wherein the second imaging and measuring device comprises a three-dimensional digital volume tomography device, a three-dimensional x-ray device, a magnetic resonance imaging (MRI) device, or a CAT scan device.

12. The system of claim 11 wherein the MRI device is a real-time device.

13. The system of claim 9 wherein a first reference position indicator of the series of reference indicators is located on one or more teeth.

14. The system of claim 13 wherein the first reference position indicator comprises a microdevice.

15. The system of claim 14 wherein the microdevice comprises a transducer.

16. The system of claim 13 wherein second and third reference position indicators of the series of reference position indicators are located on probes of the first and second imaging and measuring devices.

17. The system of claim 9 wherein the processor registers a location and orientation of a second reference position with respect to a first reference position from the position data received from the positioning system, and an orientation of resulting individual frames of measurements in the reference system.

18. The system of claim 9 wherein the processor registers a location and orientation of a first reference position indicator with respect to a second reference position indicator and an orientation of resulting individual frames of measurements in the reference system.

19. The system of claim 9 wherein a reference position indicator of the series of reference indicators comprises an active device.

20. The system of claim 9 wherein a reference position indicator of the series of reference indicators comprises a passive device.

21. The system of claim 9 wherein a reference position indicator of the series of reference indicators comprises both active and passive devices.

22. The system of claim 9 wherein the image data stored in the data collection device is used by the processor to generate a virtual model of a jaw.

23. The system of claim 22 wherein the virtual model of the jaw comprises a unit emulating mechanics of TMJ and wherein the jaw simulates jaw movements.

24. The system of claim 23 wherein the jaw movements comprise normal and abnormal mastication.

25. The system of claim 24 wherein the normal and abnormal mastication comprise clenching and bruxing.

26. The system of claim 22 wherein the virtual model of the jaw comprises solid 3D models of intra-oral objects.

27. The system of claim 26 wherein the intra-oral objects comprise teeth, subgingival surfaces and occlusal surfaces.

28. The system of claim 9 wherein the series of reference position indicators comprise registration signal sensors, registration signal receivers, registration signal transmitters, registration signal transceivers, transducers, trackers, or a combination thereof.

29. The system of claim 9 wherein the image data received from the first and second imaging and measuring devices includes images of at least one of the series of reference position indicators, and the image of a surface appearance of a patient's teeth or the image of an internal structure and density of the patient's teeth.

30. A method of manufacturing a physical model, core, or framework for a dental restoration comprising:
  measuring a surface appearance of a patient's teeth to generate an image of the surface appearance without impressions or cast models;
  measuring an internal structure of the patient's teeth to generate an image of the internal structure;
  monitoring, calculating, and recording position data associated with reference position indicators in a reference system;
  storing the image and position data;
  processing the stored image and position data by:
    orienting the image of the surface appearance in the reference system using the position data from the reference position indicators;
    orienting the image of the internal structure in the reference system using the position data from the reference position indicators;
    superimposing the image of the surface appearance on the image of the internal structure; and
  using the superimposed images of the patient's teeth, designing the new dental restoration by generating the physical model, core or framework for the new dental restoration.

31. The method of claim 30, wherein processing the stored image and position data further includes:
  generating a solid three-dimensional model from the superimposed images.

32. The method of claim 30 wherein the image of the surface appearance and the image of the internal structure include representations of at least one of the reference position indicators.

* * * * *